United States Patent [19]

Fenton

[11] Patent Number: 4,574,158

[45] Date of Patent: * Mar. 4, 1986

[54] ACETAL PURIFICATION USING PHASE TRANSFER CATALYSTS

[75] Inventor: Jeff T. Fenton, Ponca City, Okla.

[73] Assignee: Conoco Inc., Ponca City, Okla.

[*] Notice: The portion of the term of this patent subsequent to Dec. 27, 2000 has been disclaimed.

[21] Appl. No.: 438,071

[22] Filed: Nov. 1, 1982

[51] Int. Cl.$^4$ .......................................... C07D 321/00
[52] U.S. Cl. ................... 549/347; 549/357; 549/368; 549/369; 568/594
[58] Field of Search ............... 549/368, 369, 347, 357; 568/594

[56] References Cited

U.S. PATENT DOCUMENTS

| | | | |
|---|---|---|---|
| 3,149,127 | 9/1964 | Platz | 549/368 |
| 3,470,208 | 9/1969 | Lasco et al. | 549/368 |
| 3,519,650 | 7/1970 | Fleck et al. | 549/368 |
| 3,580,928 | 2/1968 | McAndrew et al. | 568/594 |
| 3,607,882 | 9/1971 | Wenger | 549/368 |
| 3,849,444 | 11/1974 | Fuchs et al. | 549/347 |
| 4,026,873 | 5/1977 | Iguchi | 549/368 |
| 4,332,644 | 6/1982 | Hamanaka et al. | 549/368 |
| 4,423,238 | 12/1983 | Fenton | 549/368 |
| 4,513,144 | 4/1985 | Fenton | 549/347 X |

FOREIGN PATENT DOCUMENTS

| | | | |
|---|---|---|---|
| 557949 | 5/1958 | Canada | 549/347 |
| 1046008 | 12/1958 | Fed. Rep. of Germany | 568/594 |
| 2806853 | 8/1978 | Fed. Rep. of Germany | 549/368 |
| 0006272 | 4/1966 | Japan | 549/368 |
| 0025502 | 11/1968 | Japan | 549/368 |

OTHER PUBLICATIONS

Chem. Abstract 54: 7932b, (1960).

*Primary Examiner*—Ethel G. Love
*Attorney, Agent, or Firm*—Cortlan R. Schupbach

[57] ABSTRACT

Trioxane and other acetals are purified by contact with an alkali metal hydroxide and phase transfer catalyst followed by isolation in a purified form. This reaction provides acetals sufficiently pure for polymerization to high molecular weight.

7 Claims, No Drawings

ACETAL PURIFICATION USING PHASE TRANSFER CATALYSTS

This invention relates to an inexpensive and simple method for obtaining acetals in purified form. More specifically, this invention relates to a method for obtaining acetals in purified form rapidly and inexpensively by contacting said acetals with an alkali metal hydroxide and a phase transfer catalyst, then recovering the purified acetal.

Trioxane, which is the cyclic trimer of formaldehyde, is normally manufactured by heating aqueous formaldehyde solutions in the presence of a strong mineral acid such as sulfuric or hydrochloric acid. Unfortunately, the trioxane recovered from such a process contains impurities. These impurities include water, formic acid, methanol, methylal, methyl formate and the like. When trioxane containing these impurities is polymerized, some of the impurities act as chain transfer agents, thereby causing the resulting polymer product to have a lower molecular weight than otherwise possible when these impurities are absent. The molecular weight of the oxymethylene polymer obtained decreases as the amount of these impurites contained in the monomer feed increases. Impurities in trioxane can reach concentrations such that polymerization is severely retarded.

The major use for these acetals is in polymerization reactions. The presence of a small amount, such as 100 parts per million of these impurities in the monomer feed causes sufficient chain transfer reactions to occur that the resulting molecular weight is not sufficiently high to provide a useful polymer.

Initially, attempts were made to purify acetals by distillation and recrystallization. However, such purification schemes do not sufficiently reduce the amount of impurities contained in the acetals to provide improved polymerization reactions unless such polymerizations and recrystallizations are carried out under stringent conditions and repeated several times, all of which make such a process economically prohibitive on a commercial basis.

Many attempts have been made in the art to improve the process for purifying acetals. U.S. Pat. No. 4,026,873 teaches polyoxymethylene crystals prepared from trioxane wherein prior to polymerization the trioxane is purified by refluxing in the presence of sodium wire. U.S. Pat. No. 3,580,928 teaches a process for purifying acetals where the acetal is purified by contacting with liquid sodium, a precipitate is allowed to form and then removed from the solution. U.S. Pat. No. 3,607,882 deals with a method of removing impurities of trioxane and other acetals by forming an alkali metal ketyl which remains as a bottom after separation via distillation, to provides a purified acetal. However, this method is unsuitable since large quantities of ketones are required and large amounts of residue remain unless great care is taken. In addition, it has been found that attempts to use this procedure results in unpredictable quality during the removal of the impurities.

U.S. Pat. No. 3,519,650 and European patent application No. 36552 relates to the purification of trioxane by treating the trioxane with an aqueous alkaline reagent such as sodium hydroxide and potassium hydroxide. U.S. Patent No. 3,149,127 treats impure trioxane with potassium oxide. U.S. Pat. No. 3,560,526 treats substituted trioxane with sodium oxide. U.S. Pat. No. 3,281,336 purifys-trioxane by extractively distilling the same with ethylene or propylene glycol. However, all of these methods are unsuitable from a quality or cost effectiveness standpoint.

It would therefore be of great benefit to provide an improved method wherein a rapid, economical removal of impurities from acetal such as trioxane can be carried out.

It is therefore an object of the present invention to provide an improved process for the removal of impurities from acetals such as trioxane. Other objects will be apparent to those skilled in this art as the description proceeds.

The alkali metal hydroxides of the present invention have the general formula MOH wherein M represents any alkali metal. In addition, an effective amount of a phase transfer catalyst is added to the reaction mixture. The invention is not effective using alkali metal hydroxides in the absence of a phase transfer catalyst. The amount of alkali metal hydroxide and phase transfer catalysts used will vary depending on the level of impurities, the length of contact time and temperature during the contact time.

After the impurities have been reduced, utilizing the alkali metal hydroxide and phase transfer catalyst, acetals can be recovered by any conventional technique. Examples of conventional techniques known to those skilled in the art are filtration, distillation, flash distillation and the like, with flash distillation being the preferred technique. Purified acetals are then suitable for any desired purpose, but are especially useful for polymerization to high molecular weight.

I have discovered the use of phase transfer catalysts with alkali metal to purify acetals in my copending patent application U.S. Ser. No. 378,660, filed May 17, 1982, now U.S. Pat. No. 4,423,238. However phase transfer catalysts in that invention were used to enhance already known techniques, whereas in the present invention phase transfer catalysts activate a normally inactive material.

The present invention can be carried out quickly and easily, but must be carried out under substantially anhydrous conditions. It would, of course, be preferable to carry out the present invention under a dry inert atmosphere, but an inert atmosphere is not critical to the success of the present invention.

After the impurities have been reduced utilizing alkali metal hydroxides, the alkali metal residues remain behind with the impurity residues after filtration or fractional distillation. The resultant recovered acetals are extremely pure and useful.

Normally, the process of the instant invention is carried out at a temperature sufficient to place the acetals to be purified in a molten state. Any temperature above this may be used as desired, but it is clearly more convenient to utilize the lowest temperature consistent with maintaining the acetals in a molten condition.

The process of the present invention can be carried out for a time ranging from about 15 minutes to about 24 hours, but normally times ranging from about 1 hour to about 5 hours will be used and times ranging from about 1 hour to about 2 hours is preferred.

Normally, from about 0.5 to about 10 weight percent of alkali metal hydroxide, based on the weight of acetal present, will be used, but from about 1 to about 5% is preferred.

In addition to the alkali metal hydroxides used, phase transfer catalysts are normally used in an amount at least equal to alkali metal hydroxides used, but can be used in amounts up to about 10% by weight.

Although I do not wish to be bound, I believe a 1:1 complex forms between the phase transfer catalyst and the alkali metal hydroxide. The phase transfer catalyst is not destroyed in the reaction, and is thus useful for subsequent purifications. Therefore, a ratio of from about 10:1 to about 1:1 alkali metal hydroxide to phase transfer catalyst respectively can be used. Mixtures of alkali metal hydroxides and mixtures of phase transfer catalysts can be used.

Acetals which can be purified using the process of the present invention are those having the general structure

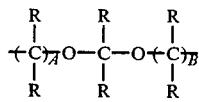

wherein A and B are numbers from about 1 to about 3, R is hydrogen or a hydrocarbon radial having from 1 to about 20 carbon atoms, cyclic aliphatic or aromatic radicals having from 6 to about 20 carbon atoms, or mixtures of these. The present invention comprises contacting said trioxane or acetal or mixtures of these with an alkali metal superoxide, optionally in the presence of a phase transfer catalyst, refluxing for a time sufficient to react with impurities present, and removing the reduced alkali metal, and phase transfer catalyst is used.

Representative examples of acetals which may be purified using the method of the present invention are trioxane, tetraoxane, 1,3-dioxane, 3-dioxane, 4-methyl 1,3-dioxolane, 1,3,5-trioxacyclooctane, 1,4-butane-diolformal, 1,4-butenediolformal, methoxymethylal, methylal and dimethoxymethylal. The present invention is especially effective with trioxane, which is polymerizable in and of itself or can be copolymerized with other monomeric compounds to form polyoxymethylene polymers and copolymers.

The acetals treated using the method of the present invention can contain high amounts of impurities, i.e. 5 weight percent or more based upon the weight of the acetal. Normally, as produced, such acetals will contain from about 0.05 to about 5.0 weight percent of such impurities. Water and methanol are usually the predominant impurities.

The alkali metal hydroxides useful in the present invention have the formula MOH where M is sodium, potassium and lithium, and of these sodium and potassium are more preferred with potassium being the most preferred metal. Mixtures of metal hydroxides may also be used, for example sodium potassium hydroxides.

The invention functions more rapidly and efficiently than the prior art processes when carried out in the presence of a phase transfer catalyst. Examples of phase transfer catalysts useful in the present invention are crown ethers, cryptates and quaternary salts.

Both macrocyclic (crown ether) materials and macrobicyclic (cryptate materials) are useful in the practice of the present invention. These materials are normally extremely complex and have no encompassing general formulas. However, representative but non-exhaustive examples of crown ethers useful in the practice of the present invention include 15-crown-5-ether, 18-crown-6-ether, dibenzo-18-crown-6 ether, dicyclohexyl-18-crown-6-ether, benzo-15-crown-5 ether, alkyl-18-crown-6-ether, alkyl-2,2,2-cryptate ether, benzo-2,2,2-cryptate, 2,2,2-cryptate, 2,2,1-cryptate, 2,11-cryptate, dibenzo-24-crown-6, and 12-crown-4.

Crown ethers are chosen depending on the alkali metal used. That is, 12-crown-4 is best for Lithium, 15-crown-5 for sodium, and 18-crown-6 for potassium. Mixtures of metals would require, optimally, a mixture of crown ethers. Cryptates and polyethers are less specific since they contain flexible linkages allowing these materials to "wrap" around the metal ion.

In addition, analogues of crown ethers and cryptates containing nitrogen or sulfur atoms are also useful in the practice of the present invention as they have donor properties to the crown ethers containing only carbon oxygen in the linkages. Representative examples of structures of such analogues are described.

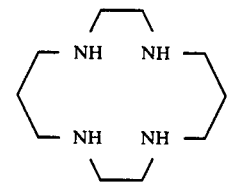

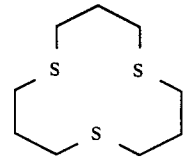

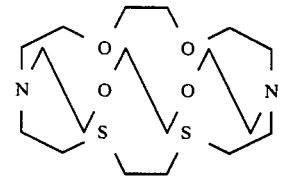

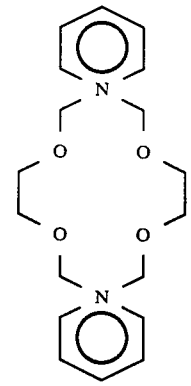

Polyethers of the general formula

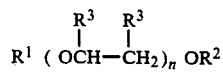

where $R^1$, $R^2$, and $R^3$ are, independently, hydrogen atoms or alkyl radicals containing from 1 to 20 carbon atoms and n is greater than 1 are useful as phase transfer catalysts in the present invention.

Representative but non-exhaustive examples of polyethers useful in the present invention are polyethylene glycol of varying molecular weight of the formula HO-(CH$_2$CH$_2$O)$_n$H where n is from 1 to 14, glyme, diglyme, triglyme, tetraglyme, propylene glycol methyl ether, diethylene glycol methyl ether, diethylene glycol n-butylether. Mixtures of these catalysts can be used.

Also useful are quaternary salts of the general formula X(MR$^1$R$^2$R$_3$R$^4$) where M is nitrogen, phosphorus, arsenic antimony or bismith, X is an anion which will dissociate from the cation in an aqueous environment, and R$^1$, R$^2$, R$^3$ and R$^4$ are monovalent hydrocarbon radicals consisting of alkyl, alkenyl, aryl, alkaryl, aralkyl and cycloalkyl radicals. X is preferably halide and hydroxyl ions. Generally each R can contain from about 1 to about 25 or more carbon atoms each. The total carbon atom content of all these groups has no theoretical upper limit, although about 70 carbon atoms constitutes a product having a practical upper limit imposed by economic factors. It is also highly preferred that each of the hydrocarbon substituents R$^1$, R$^2$, R$^3$, and R$^4$, contain more than a single carbon atom.

Representative but non-exhaustive examples of suitable quaternary salts are hexadecyltrihexylammonium bromide; trioctylethylammonium bromide; tridecylmethylammonium chloride; didodecyldimethylammonium chloride; tetraheptylammonium iodide; dioctadecyldimethyl ammonium chloride; tridecylbenzylammonium chloride; ditricosylmethylammonium chloride, tributyldecylphosphonium iodide; triphenyldecylphosphonium iodide, tributylhexadecylphosphonium iodide; tricaprylyldodecylammonium p-toluene sulfonate; tribenzyldecylarsonium chloride; tetranonylammonium hydorxide; tritridecylphenylstibonium chloride; triahentriacontylmethylbismuth chloride; N,N,N'N'-tetramethyl-N,N'-ditetradecyl-p-xylene -α,α'-diammonia dichloride; 1-methyl-1-(N-octadecanoyl-2-minoethyl)2-heptadecyl-4,5-dihydro-1,3-diazole methylsulfate; N,N,N',N'-tetramethyl-N,N'-dioctadecyl-x-dodecyl-y-xylene α,α'-diammonium dichloride; N,N-dioctadecyl-N-methyl-N-(sodiocarboxylmethyl)-ammonium chloride, N,N,N',N'-tetramethyl-N,N'-dioctadecyl-p-xylene-αα'-diammonium dichloride; N,N,N',N'-tetramethyl-N,N'-dioctadecyl-1,2-ethyl-diammonium dibromide; N,N'-dimethyl-N,N,N',N'-tetraheptadecyl-2-butene-1,4-diammonium chloride.

Normally, the impurities are converted to alkali salts which are normally solids and can be separated from the acetal by sedimentation, filtration, distillation and the like. However, depending upon the phase transfer catalyst used, normally distillation or fractionation is the preferred method since these methods remove the catalysts from the system with reduced alkali metal. However, the process of the present invention requires only one distillation to be totally effective in removing sufficient impurities to allow polymerization to proceed to high levels.

The invention is more concretely described with reference to the examples below wherein all parts and percentages are by weight unless otherwise specified. The examples are provided to illustrate the present invention and not to limit it.

EXAMPLE 1

Commercial trioxane, 226 g, was placed in a 3-neck round bottom flask fitted with a Friedrichs condensor, flushed with argon, melted, and refluxed with stirring for 4.5 hours. An air-cooled condensor was attached and 204.2 g were removed by distillation into a dry, argon flushed, one liter jacketed resin kettle. The distilled trioxane was melted by 70° C. circulating water to a clear melt, and thereafter 6.8 ml of ethylene oxide (2.97 wt. % based on trioxane) were added to the kettle. To the stirred melt was added 3.6 ml of a 0.03113M solution of BF$_3$.OEt$_2$ in anhydrous methylene chloride. After 1 hour 45 minutes, no polymerization reaction occurred.

EXAMPLE 2

Commercial trioxane, 225 g, was placed in a dry, Ar flushed round bottom flask fitted with a Friedrichs condensor. To this was added 10 g of potassium hydroxide and the trioxane was refluxed with stirring for 4 hours. Then, an air-cooled condensor was added and 173.1g were distilled into a dry, Ar flushed resin kettle. The distilled trioxane was melted at 70° C. to a clear melt and 5.8 ml (2.98 wt %, based on trioxane) of ethylene oxide was added. To initiate reaction, 3.1 ml of a 0.03113M solution of BF$_3$.OEt$_2$ in anhydrous methylene chloride was added. However, after 1 hour 45 minutes, no apparent reaction had occurred.

EXAMPLE 3

To 225 g of Commercial trioxane (225 g) in an argon flushed flask with Friedrichs condensor was mixed with 10 g of KOH and 10 g of polyethylene glycol (molecular weight=600). This mixture was refluxed for 4 hours with stirring and then 197.0 g were distilled into a dry, argon flushed resin kettle. The distilled trioxane was melted at 70° C. and mixed with 6.6 ml (2.98 wt %) ethylene oxide. The reaction was initiated with 3.5 ml of a 0.03113M BF$_3$.OEt$_2$ in methylene chloride solution and after 54 minutes it had polymerized to a solid mass. The inherent viscosity of the resultant copolymer was 0.24 dl/g.

EXAMPLE 4

Commercial trioxane is refluxed for from ca. 0.5-24 hours over a mixture of ca. 5-10 g potassium hydroxide and 0.5-5 g of polyethylene glycol (HO—CH$_2$CH$_2$O)-$_n$—H, n=3) under an inert atmosphere. After reflux, the trioxane is distilled and condensed. Upon melting, the trioxane shows no signs of polymer formation and hence is of high purity.

While certain embodiments and details have been shown for the purpose of illustrating this invention, it will be apparent to those skilled in this art that various changes and modifications may be made herein without departing from the spirit or scope of the invention.

I claim:
1. A method for purifying acetals comprising
 (1) placing acetals in a molten state
 (2) contacting said acetals with alkali metal hydroxide and a phase transfer catalyst for a time sufficient to reduce impurities present, and
 (3) recovering the purified acetal
2. A method as described in claim 1 wherein the acetals are contacted for a time ranging from about 15 minutes to about 24 hours in the presence of from about 0.5 to about 20 weight percent alkali metal hydroxide, and from about 0.01 to about 20 weight percent phase transfer catalyst, all based on the weight of acetal present.
3. A method as described in claim 2 wherein the acetal is at least one material selected from the group consisting of trioxane, tetraoxane, 1,3-dioxane, 4-methyl 1,3-dioxane, 1,3-dioxolane, 1,3,6-trioxacyclooctane, 1,4- butane-diolformal, 1,4-butenediolformal, methoxymethylal, methylal and dimethoxymethylal.

4. A method as described in claim 3 wherein the phase transfer catalyst is at least one crown ether selected from the group consisting of 15-crown-5-ether, 18-crown-6-ether, dibenzo-18-crown-6 ether, dicyclohexyl-18-crown-6-ether, benzo-15-crown-5-ether, alkyl-18-crown-6-ether, alkyl-2,2,2-cryptate ether, benzo-2,2,2-cryptate, 2,2,2-cryptate, 2,2,1-cryptate, 2,1,1-cryptate, dibenzo-24-crown-6, and 12-crown-4.

5. A method as described in claim 3 wherein the phase transfer catalyst is at least one polyether selected from the group consisting of HO—$(CH_2CH_2O)_n$H where n is from 1 to 14, glyme, diglyme, triglyme, tetraglyme, propylene glycol methyl ether, diethylene glycol, methyl ether, and diethylene glycol n-butyl ether.

6. A method as described in claim 3 wherein the phase transfer catalyst is at least one quaternary salt selected from the group consisting of hexadecyltrihexylammonium bromide; trioctylethylammonium bromide; tridecylmethylammonium chloride; didodecyldimethylammonium chloride; tetraheptylammonium iodide; dioctadecyldimethyl ammonium chloride; tridecylbenzylammonium chloride; ditricosylmethylammonium chloride, tributyldecylphosphonium iodide; triphenyldecylphosphonium iodide, tributylhexadecylphosphonium iodide; tricaprylyldodecylammonium p-toluene sulfonate; tribenzyldecylarsonium chloride; tetranonylammonium hydroxide; tritridecylphenylstibonium chloride; triahentriacontylmethyl-i bismuth chloride; N,N,N′N′-tetramethyl-N,N′-ditetradecyl-p-xylene-α,α′-diammonia dichloride; 1-methyl-1-N-octadecanoyl-2-minoethyl)2-heptadecyl-4,5-dihydro-1,3-diazole methylsulfate; N,N,N′,N′-tetramethyl-N,N′-dioctadecyl-x-dodecyl-y-xylene, α,α′-diammonium dichloride; N,N-dioctadecyl-N-methyl-N-(sodiocarboxylmethyl)-ammonium chloride, N,N,N′,N′-tetramethylN,N′-dioctadecyl-p-xylene-α,α′-diammonium dichloride; N,N,N′,N′-tetramethyl-N,N′-dioctadecyl-1,2-ethyl-diammonium dibromide; N,N′-dimethyl-N,N,N′,N′-tetraheptadecyl-2-butene-1,4-diammonium chloride.

7. A method as described in claim 3 wherein the alkali metal is potassium hydroxide and the phase transfer catalyst is polyethylene glycol.

* * * * *